United States Patent
Zeng et al.

(10) Patent No.: US 9,132,281 B2
(45) Date of Patent: Sep. 15, 2015

(54) FOCUSED RADIATION FOR AUGMENTING IMMUNE-BASED THERAPIES AGAINST NEOPLASMS

(75) Inventors: Jing Zeng, Rockville, MD (US); Charles George Drake, Baltimore, MD (US); Drew M. Pardoll, Brookeville, MD (US); Michael Lim, Reisterstown, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/127,597

(22) PCT Filed: Jun. 19, 2012

(86) PCT No.: PCT/US2012/043124
§ 371 (c)(1),
(2), (4) Date: Feb. 26, 2014

(87) PCT Pub. No.: WO2012/177624
PCT Pub. Date: Dec. 27, 2012

(65) Prior Publication Data
US 2014/0155678 A1  Jun. 5, 2014

Related U.S. Application Data

(60) Provisional application No. 61/499,237, filed on Jun. 21, 2011, provisional application No. 61/549,975, filed on Oct. 21, 2011.

(51) Int. Cl.
G21K 5/04 (2006.01)
A61N 5/10 (2006.01)
(Continued)

(52) U.S. Cl.
CPC ........ *A61N 5/1001* (2013.01); *A61K 39/39558* (2013.01); *A61K 41/00* (2013.01);
(Continued)

(58) Field of Classification Search
USPC ......... 250/492.1, 492.2, 492.3; 600/1, 2, 3, 4, 600/5
See application file for complete search history.

(56) References Cited

U.S. PATENT DOCUMENTS

| | | |
|---|---|---|
| 7,481,758 B2 | 1/2009 | Weil et al. |
| 2010/0094119 A1 | 4/2010 | Yu et al. |
| 2011/0224141 A1* | 9/2011 | Thompson et al. .......... 514/10.4 |

FOREIGN PATENT DOCUMENTS

| | | |
|---|---|---|
| WO | 2010107486 A2 | 9/2010 |
| WO | 2010132389 A2 | 11/2010 |
| WO | 2011019630 A2 | 2/2011 |

OTHER PUBLICATIONS

Zeng, J., et al., "Combining anti-PD-1 (B7-H1) Immunotherapy with Stereotactic Radiosurgery in a Mouse Orthotopic Glioblastoma Model", International Journal of Radiation Oncology Biology Physics, Oct. 1, 2011, vol. 81, Issue 2, Supplement, pp. S82 and S83.
(Continued)

*Primary Examiner* — Nicole Ippolito
(74) *Attorney, Agent, or Firm* — Johns Hopkins Technology Transfer

(57) ABSTRACT

An approach combining immune-based therapies with focused radiation, including stereotactic radiation, to treat cancers is disclosed. The use of focused radiation primes the immune system in a similar manner to vaccines to augment immune-based therapies and can counteract the suppressive effects of a tumor. The combination of focused radiation and immune-based therapies, including administration of at least one immunotherapeutic agent, improves survival compared to each therapy alone and can, in some cases, lead to a durable cure. Accordingly, focused radiation can be an adjuvant for immune-based therapies for treating cancers.

16 Claims, 13 Drawing Sheets

Neoadjuvant Strategy

(51) Int. Cl.
  *A61K 41/00* (2006.01)
  *C07K 16/24* (2006.01)
  *C07K 16/28* (2006.01)
  *A61K 45/06* (2006.01)
  *A61K 39/395* (2006.01)
  *A61K 39/00* (2006.01)

(52) U.S. Cl.
  CPC ............. *A61K 45/06* (2013.01); *A61N 5/1042* (2013.01); *C07K 16/24* (2013.01); *C07K 16/2818* (2013.01); *C07K 16/2878* (2013.01); *A61K 2039/505* (2013.01); *A61K 2039/507* (2013.01)

(56) References Cited

OTHER PUBLICATIONS

Buchsbaum, D., et al., "Treatment of pancreatic cancer xenografts with erbitux (IMC-C225) anti-egfr antibody, gemcitabine, and radiation", Int. J. Radiation Oncology Biol. Phys. (2002) vol. 54, No. 4, pp. 1180-1193.

Hassan, R., et al., "Tumor-directed radiation and the immunotoxin SS1P in the treatment of mesothelin-expressing tumor xenografts", Clin Cancer Res (2006) vol. 12, No. 16, pp. 4983-4988.

Hatano, K., et al., "The impact of neoadjuvant and concurrent MAB for intermediate & high risk localized prostate cancer treated with IMRT", European Journal of Cancer (2009) vol. 7, No. 2, pp. 415-416.

Johns, T., et al., "MAB 806 enhances the efficacy of ionizing radiation in glioma xenografts expressing the DE2-7 epidermal growth factor receptor" Int. J. Radiation Oncology Biol. Phys. (2010) vol. 78, No. 2, pp. 572-578.

Levy, A., "Radiation therapy and immunotherapy: implications for a combined cancer treatment" Critical Reviews in Oncology/Hematology (2013) vol. 85, pp. 278-287.

Milenic, D., "Antibody-targeted radiation cancer therapy" Nature Reviews, Drug Discovery, Nature Publishing Group, GB (2004) vol. 3, No. 6, pp. 488-499.

Newcomb, E., "The combination of ionizing radiation and peripheral vaccination produces long-term survival of mice bearing established invasive GL261 gliomas" Clinical Cancer Research (2006) vol. 12, No. 15, pp. 4730-4737.

Saleh, M., "Combined modality therapy of A431 human epidermoid cancer using anti-EGFr antibody C225 and radiation" Cancer Biotherapy & Radiopharmaceuticals (1999) vol. 14, No. 6, pp. 451-463.

European Search Report and Opinion mailed Jan. 5, 2015 for application 12803394.1 (PCT/US2012/043124) filed Jun. 19, 2012.

* cited by examiner (PRIOR ART)

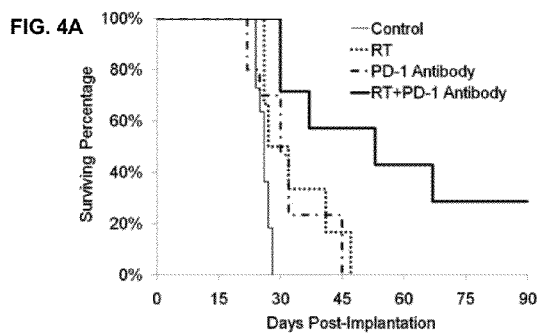
FIG. 4A
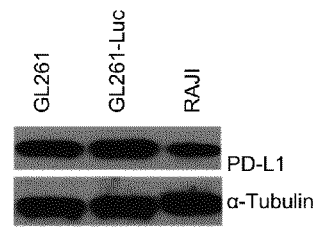
FIG. 4B
FIG. 4C
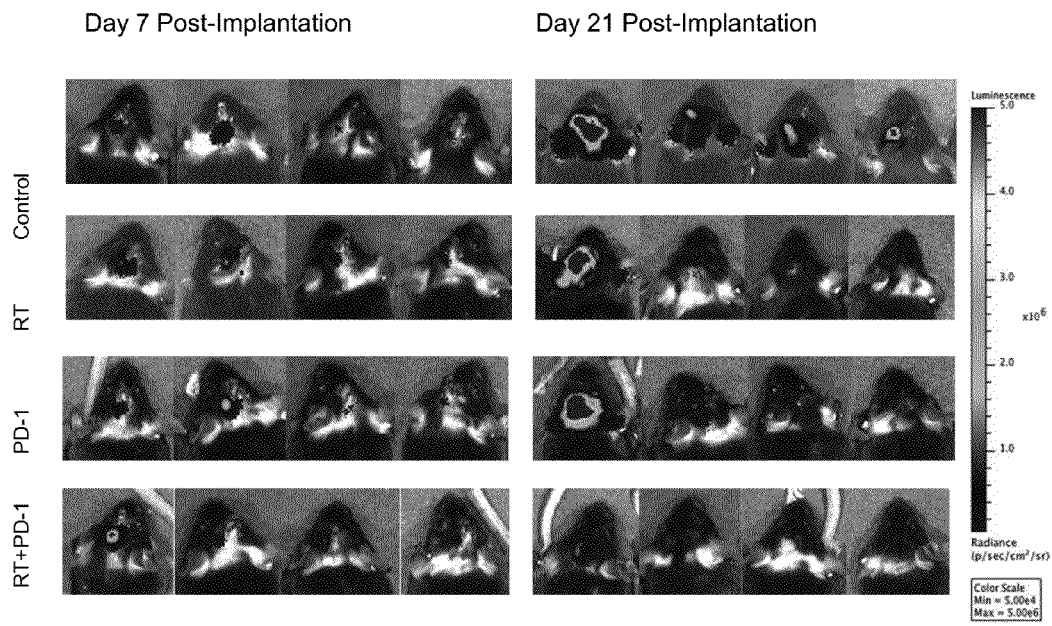

FOCUSED RADIATION FOR AUGMENTING IMMUNE-BASED THERAPIES AGAINST NEOPLASMS

CROSS-REFERENCE TO RELATED APPLICATIONS

This application is a 35 U.S.C. §371 U.S. national entry of International Application PCT/US2012/043124 having an international filing date of Jun. 19, 2012, which claims the benefit of U.S. Provisional Application No. 61/499,237, filed Jun. 21, 2011, and U.S. Provisional Application No. 61/549, 975, filed Oct. 21, 2011, the content of each of the aforementioned applications is herein incorporated by reference in their entirety.

BACKGROUND OF THE INVENTION

A central limiting factor of existing therapeutic strategies in treating neoplasms is tumor heterogeneity and the invasive nature of the tumor. Therefore, effective therapies need to specifically target a diverse and dynamic cell population, as well as attack tumor cells that have migrated beyond the margins of the tumor bulk.

For several decades, immunotherapy has been investigated as a cancer therapy. Successfully harnessing the immune response could result in a specific and adaptive anti-cancer activity at a cellular level. Immunotherapy allows for the targeting of multiple cell types in different compartments. Further, fully engaging the immune system, such as by vaccination, may provide long-term anti-cancer surveillance and protection. Accordingly, if the immune system is fully activated against a cancer the way that it becomes activated against an infection, the body can provide itself with a durable and targeted way to defend against the cancer.

Despite intensive research, however, current immunotherapy approaches have yielded disappointing results. Recent work suggests that the body can generate an antitumor immune response, yet only marginal improvements in survival have been observed. One reason for the disappointing results is the tumor immune microenvironment. Tumor cells have devised a complex set of mechanisms to evade the immune response. Cancers can mute an immune response through several mechanisms, which include, but are not limited to: downregulating the expression of the major histocompatibility complex (MHC), increasing activation of regulatory T cells ($T_{reg}$), and expressing an immunosuppressive cytokine profile. For example, tumor stem cells derived from glioblastomas cultured in bFGF and EGF more closely mirror the phenotype and genotype of primary tumors than do serum-cultured cell lines. Current methods of active immunotherapy directed to glioblastoma multiforme, as an example, are shown in FIG. 1. Tumor cells, however, can also express immune checkpoint molecules or inhibitors, such as Programmed Death 1 (PD-1), CTLA-4, B7H1, B7H4, OX-40, CD137, CD40, and LAG3, which directly inhibit immune cells and suppress the host's immune response.

Radiation therapy has been long regarded as a directly cytotoxic cancer treatment and is known to be an effective means of reducing tumor bulk. More recent evidence, however, also shows that radiation is able to counteract the immunosuppressive tumor microenvironment to generate an immune response through mechanisms, such as increased MHC class I expression, presentation of normally suppressed carcinoma-associated antigens, increased expression of pro-inflammatory cytokines, and downregulation of the Fas ligand.

Accordingly, radiation is effective in priming the immune system with cancer antigens. Current radiation strategies, however, have limitations. For example, current radiation paradigms radiate a significant margin to include infiltrating cells. This paradigm requires radiating patients for weeks and, as a result, patients have experienced radiation-associated toxicities, including a drop in the white blood cell (WBC) count, which is counterproductive for immunotherapy. In contrast, focused radiation, such as Stereotactic radiosurgery (SRS), allows for a therapeutic dose of radiation while minimizing radiation-associated toxicities. Further, a high dose of radiation can be delivered over one day with SRS.

There exists, therefore, a need for novel cancer immunotherapies which require a combination therapy approach that concurrently activates the immune system using radiation therapy, and bypasses tumor mediated immune suppression.

SUMMARY OF THE INVENTION

In accordance with an embodiment, the present invention provides a method for activating and/or maintaining an immune system against a cancer to promote an anti-tumor response in a subject, the method comprising administering to the subject a therapeutically effective dose of focused radiation to activate and/or maintain the immune system against a cancer to promote an anti-tumor response in the subject.

In accordance with an embodiment, the present invention provides a method for inhibiting, reducing, or counteracting an immunosuppressive effect of a tumor in a subject, the method comprising administering to the subject a therapeutically effective dose of focused radiation to inhibit or reduce the immunosuppressive effect of the tumor.

In accordance with an embodiment, the present invention provides a method for initiating or increasing a presence of a cancer antigen in a tumor microenvironment in a subject, the method comprising administering to the subject a therapeutically effective dose of focused radiation to initiate or increase the presence of a cancer antigen in a tumor microenvironment in the subject.

In accordance with an embodiment, the present invention provides methods for treating a tumor in a subject in need of treatment thereof, the method comprising administering to the subject a therapeutically effective dose of focused radiation to treat the tumor in combination with at least one immunotherapeutic agent.

In accordance with another embodiment, the present invention provides methods for treating a tumor in a subject in need of treatment thereof, the method comprising administering to the subject a therapeutically effective dose of focused radiation to treat the tumor in combination with at least one immunotherapeutic agent that comprises an immune checkpoint inhibitor.

In accordance with another embodiment, the present invention provides methods for treating a tumor in a subject in need of treatment thereof, the method comprising administering to the subject a therapeutically effective dose of focused radiation to treat the tumor in combination with at least one immunotherapeutic agent that is selected from the group consisting of a cytokine-based therapy, a passive immune-based strategy, including antibody therapy and adoptive therapy, and a vaccine based therapy.

In accordance with a further embodiment, the present invention provides a pharmaceutical composition comprising at least one immunotherapeutic agent, wherein the composition includes a pharmaceutically and physiologically acceptable carrier, in an amount effective for use in a medicament, and most preferably for use as a medicament for inducing an immune response, or treating cancer, or inhibiting the growth of a tumor, or neoplasm in a subject who receives or will receive focused radiation treatment, when administered to the subject in an effective amount.

In accordance with still another embodiment, the present invention provides a use of at least one immunotherapeutic agent, in the preparation of a pharmaceutical composition for the treatment of a clinical condition in an individual who receives or will receive focused radiation treatment.

In accordance with an embodiment, the present invention provides methods of neoadjuvant therapy for treating cancer in a subject in need of treatment thereof, the method comprising: (a) administering to the subject a therapeutically effective dose of focused radiation in combination with a therapeutically effective first dose of at least one immunotherapeutic agent; (b) performing surgery on the subject to remove at least a portion of a tumor associated with the cancer; and (c) administering to the subject a therapeutically effective dose of focused radiation in combination with a therapeutically effective second dose of at least one immunotherapeutic agent; wherein steps (a), (b), and (c) can be repeated in series or individually as necessary to treat the cancer in the subject. In yet further aspects, the method further comprises administering to the subject additional chemotherapy and or radiation treatment, such as conventional chemo/radiation treatment, which in some aspects also can include adjuvant therapy.

In accordance with another embodiment, the present invention provides methods of neoadjuvant therapy for treating cancer in a subject in need of treatment thereof, the method comprising: (a) administering to the subject a therapeutically effective dose of focused radiation in combination with a therapeutically effective first dose of at least one immunotherapeutic agent that is selected from the group consisting of a cytokine-based therapy, a passive immune-based strategy, including antibody therapy and adoptive therapy, and a vaccine based therapy; (b) performing surgery on the subject to remove at least a portion of a tumor associated with the cancer; and (c) administering to the subject a therapeutically effective dose of focused radiation in combination with a therapeutically effective second dose of at least one immunotherapeutic agent; wherein steps (a), (b), and (c) can be repeated in series or individually as necessary to treat the cancer in the subject. In yet further aspects, the method further comprises administering to the subject additional chemotherapy and or radiation treatment, such as conventional chemo/radiation treatment, which in some aspects also can include adjuvant therapy.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1:
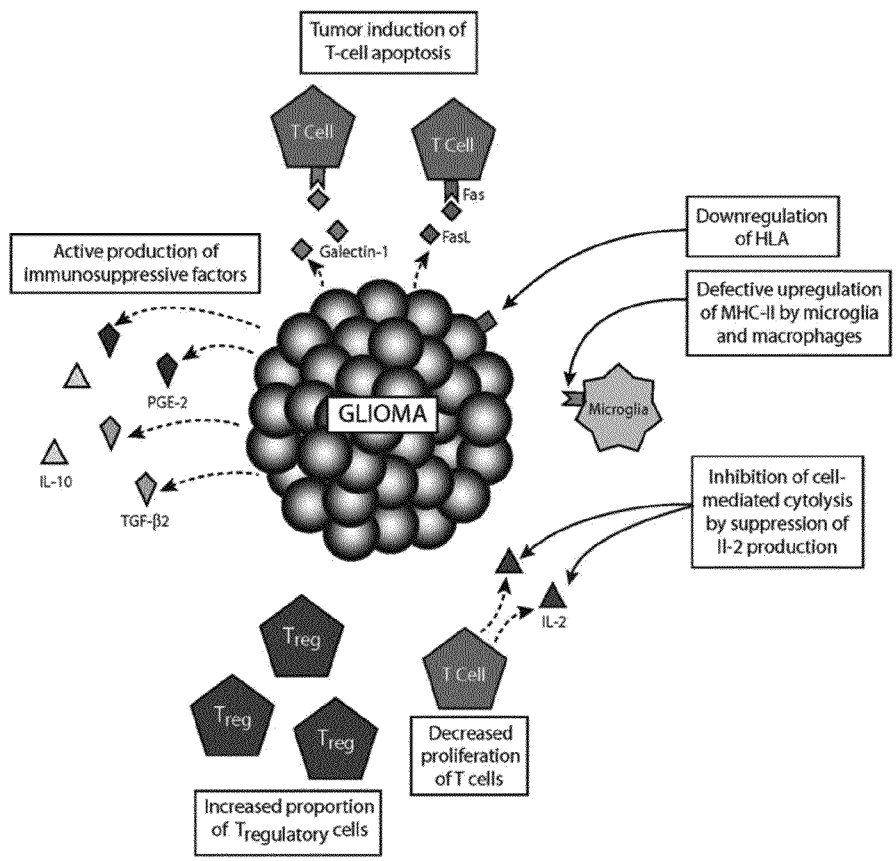
Figure 3A:
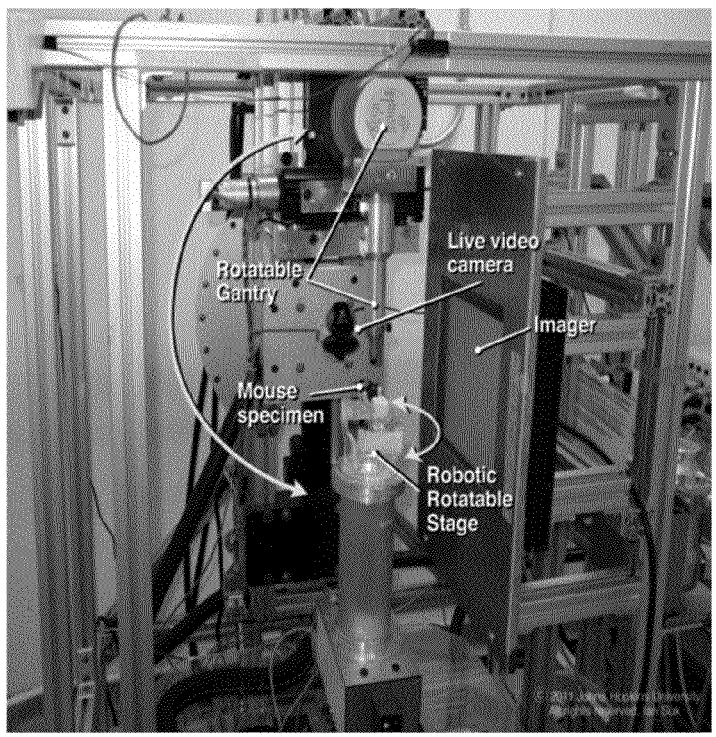
Figure 3C:
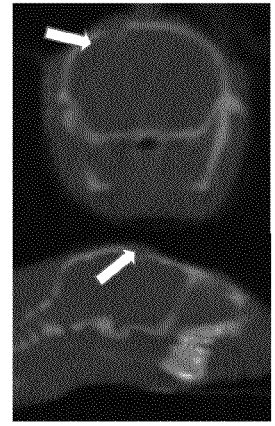
Figure 3B:
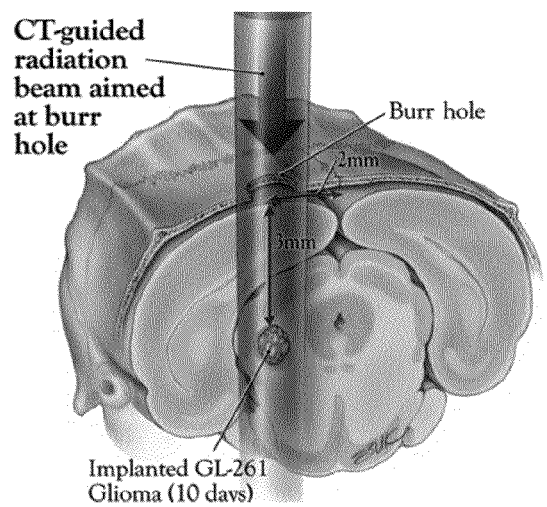
Figure 5A:
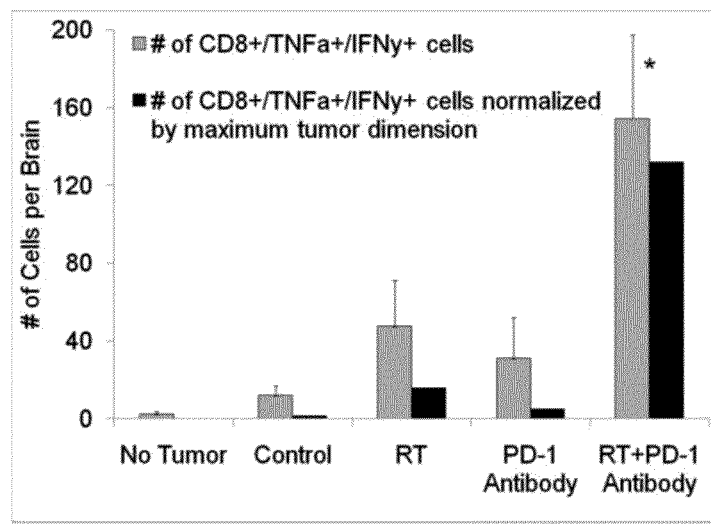
Figure 5B:
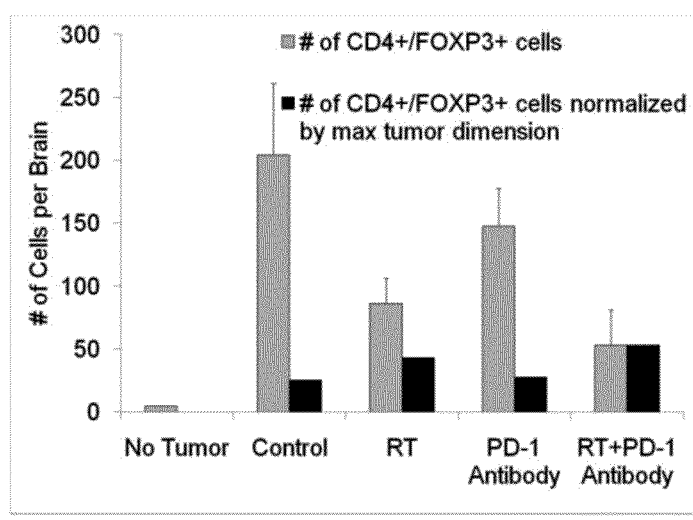
Figure 5C:
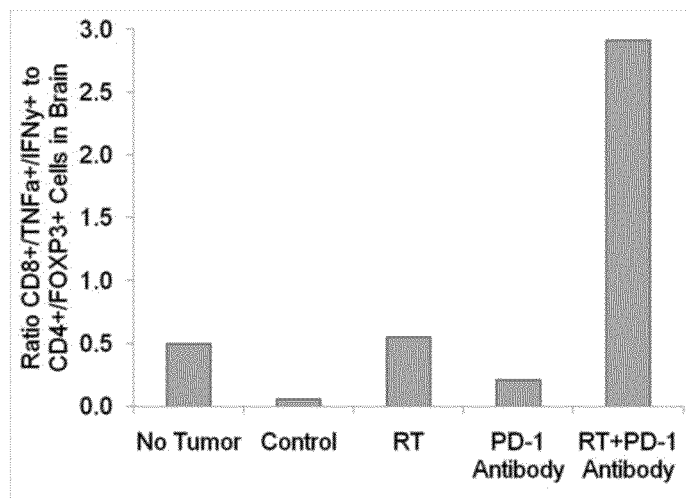
Figure 6A:
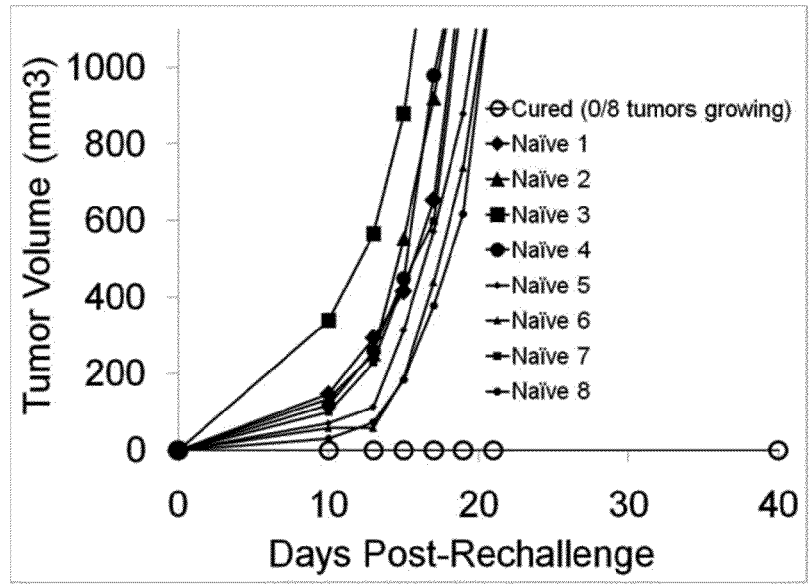
Figure 6B:
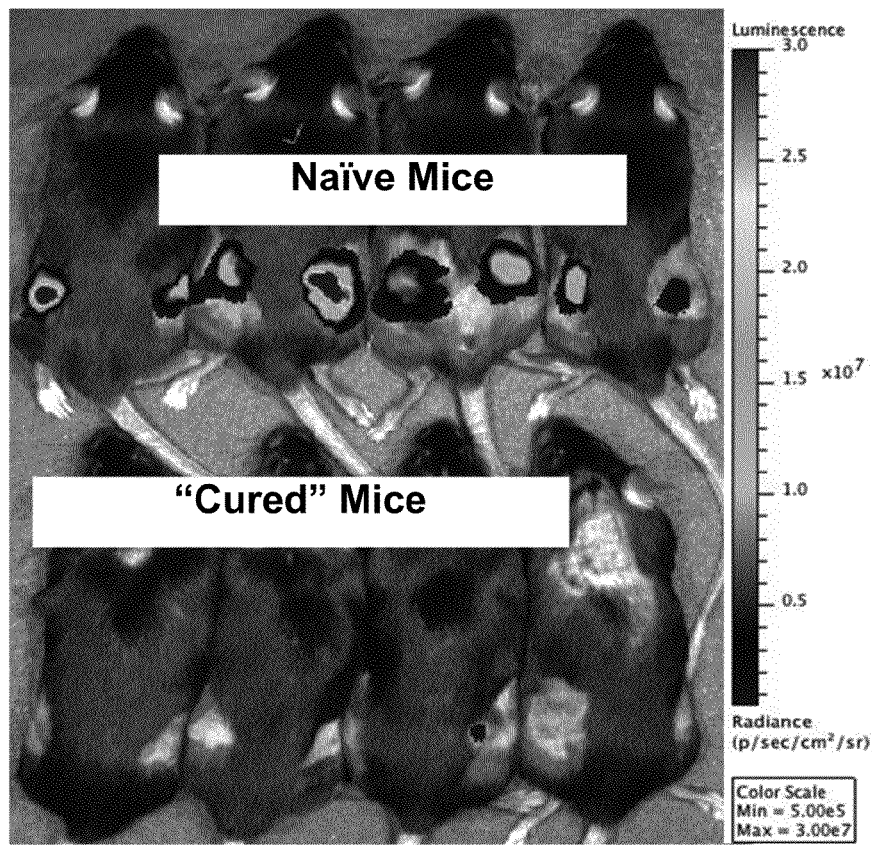

Having thus described the presently disclosed subject matter in general terms, reference will now be made to the accompanying figures, which are not necessarily drawn to scale, and wherein:

FIG. 1 provides mechanisms of immune evasion in the tumor microenvironment (PRIOR ART from Bower et al.);

FIGS. 2A-2D show intracranial implantation (2A and 2B) and histology (2C and 2D) on day-10 post-implantation;

FIGS. 3A-3C show (3A) a small animal research radiator platform (SARRP) and stereotactic radiation beam centered around the tumor based on burr-hole from implantation (3B and 3C);

FIGS. 4A-4C show (4A) Kaplan-Meier survival curves for mice in different treatment arms; (4B) western data confirming PD-L1 expression in GL161 cell line; and (4C) bioluminescent images pre- and post-treatment for mice in different treatment arms;

FIGS. 5A-5C show brain immunologic status on day-21 post-implantation: (5A) cytotoxic T-cells; (5B) regulatory T-cells; and (5C) ratio of cytotoxic to regulatory T-cells. N=3 mice in the No Tumor arm, all other arms have 6-9 mice per arm. Asterisk represents statistically significant difference between indicated treatment arm and all other treatment arms;

FIG. 6 depicts the flank-rechallenge of mice "cured" of brain tumors, compared with "naïve" mice. In 6A a graph shows increase in tumor volume of naïve ve mice versus treated. 6B shows bioluminescent imaging at day-21 of the naïve mice vs. treated.

Figure 7:
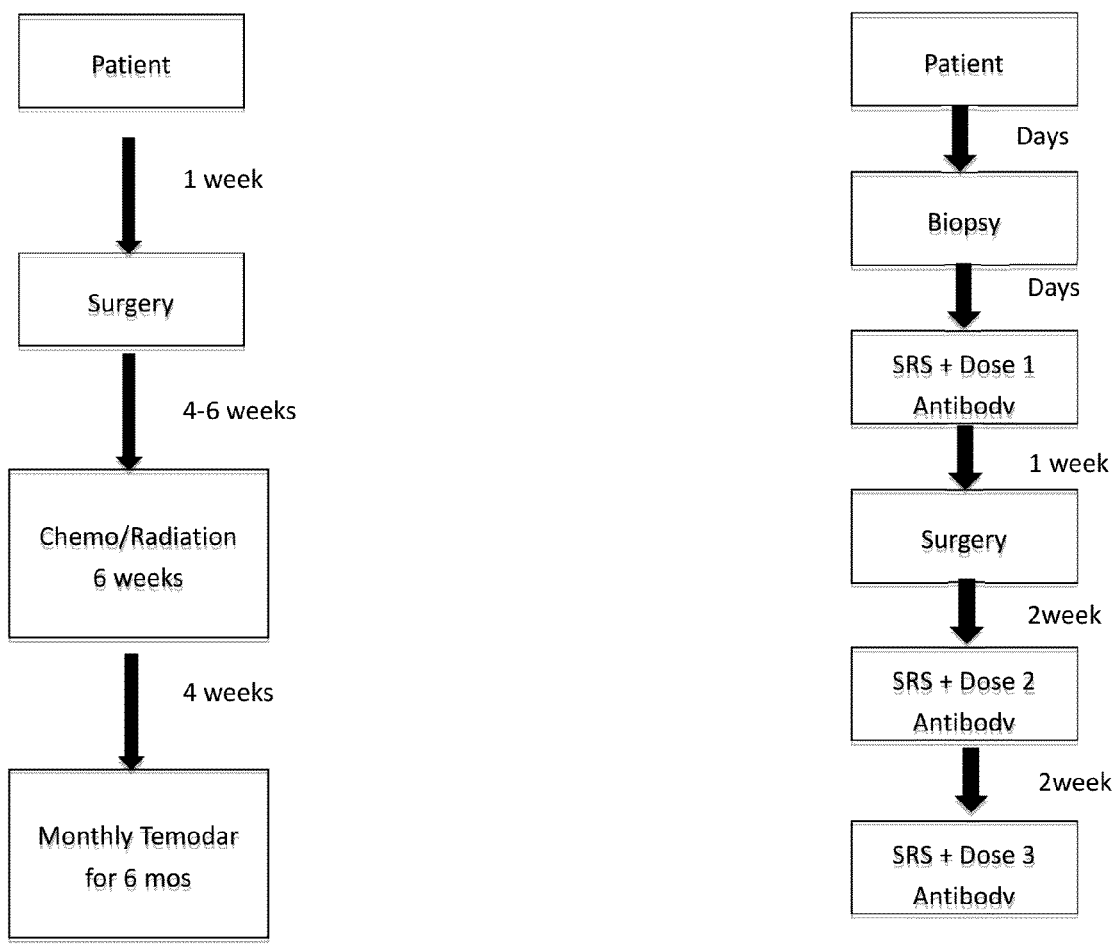

FIG. 7 is a schematic representation of a representative neoadjuvant treatment strategy utilizing the presently disclosed methods.

Figure 8:
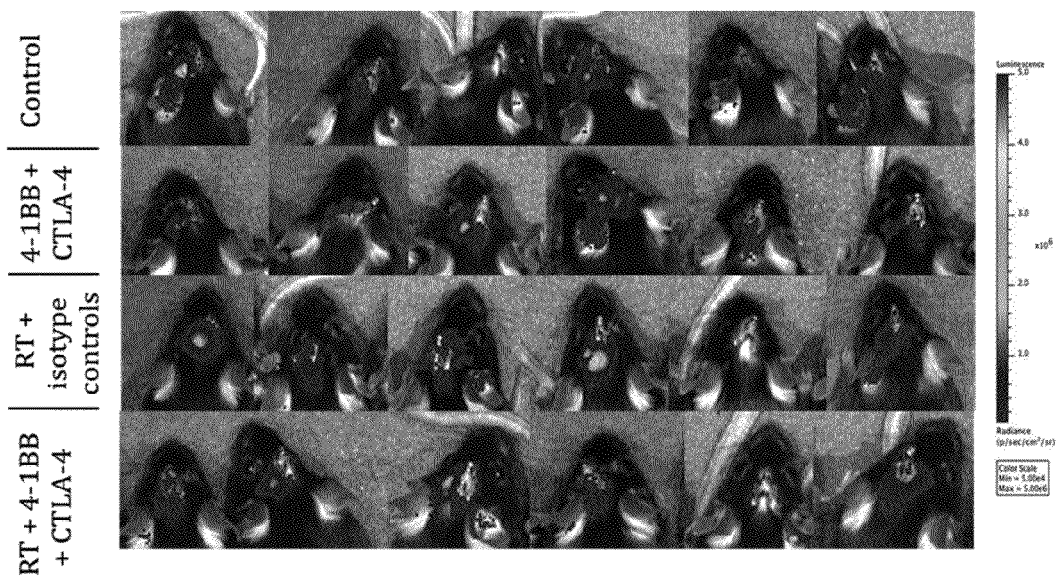

FIG. 8 shows that on day 7 after implantation, mice were stratified into four treatment groups using bioluminescent imaging: (1) isotype controls (2) stereotactic radiation (3) anti-4-1BB and anti-CTLA-4 antibodies (4) stereotactic radiation with anti-4-1BB and anti-CTLA-4 antibodies.

Figure 9:
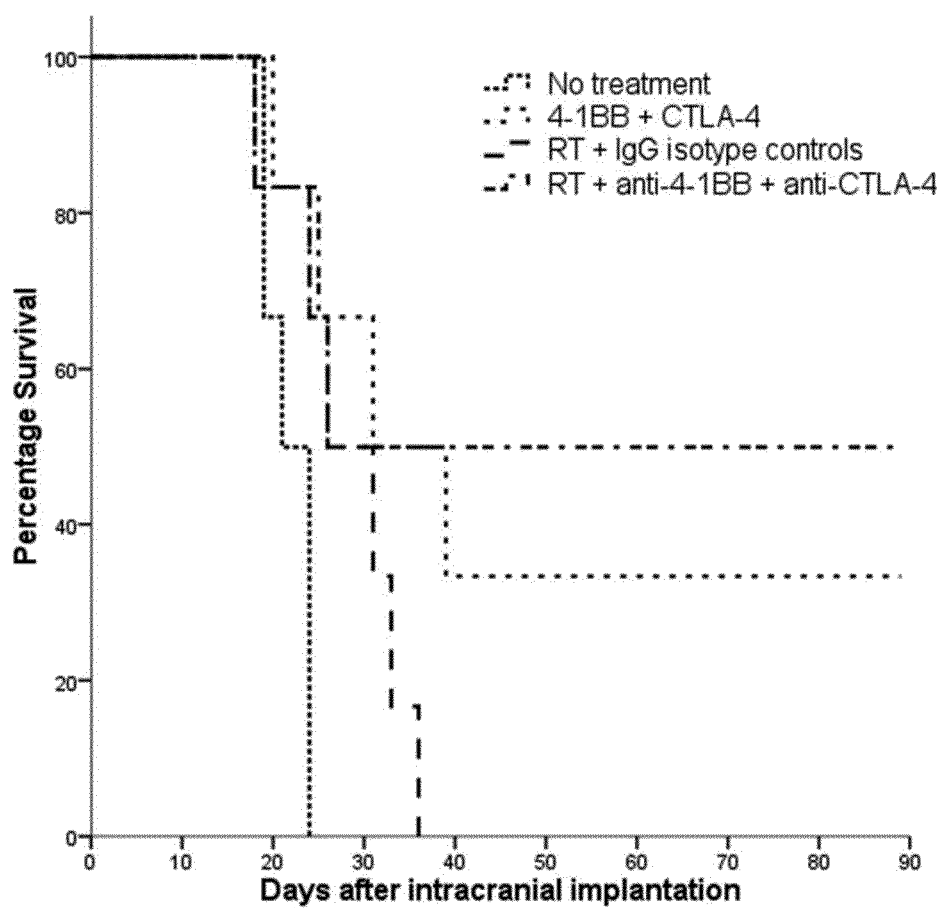

FIG. 9 depicts Kaplan-Meier curves showing mice treated with stereotactic radiosurgery combined with anti-4-1BB and anti-CTLA-4 antibodies resulted in a significantly ($P<0.05$, log rank test) higher median survival than the controls and radiation with IgG isotypes.

Figure 10A:
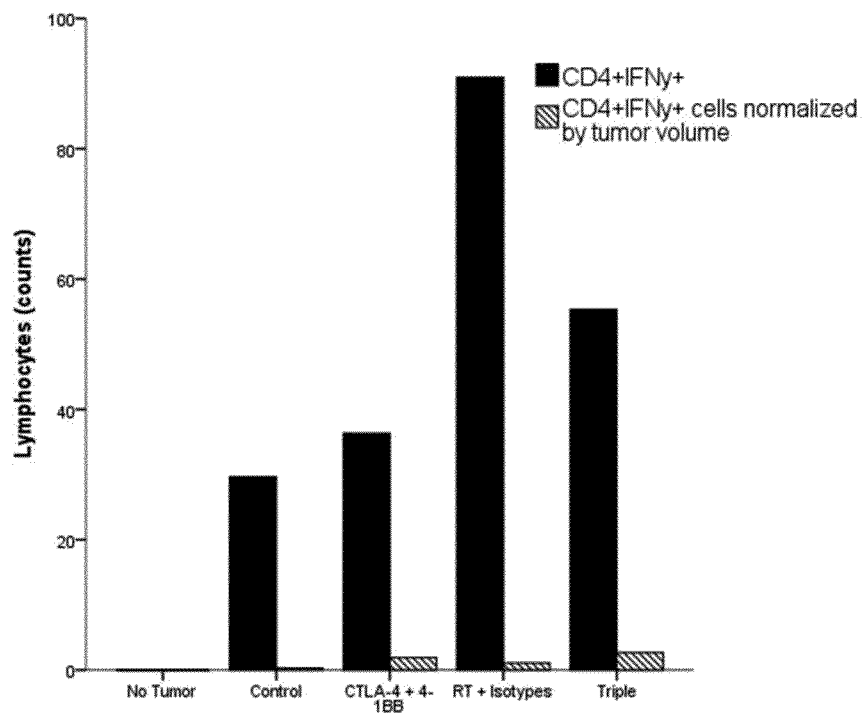
Figure 10B:
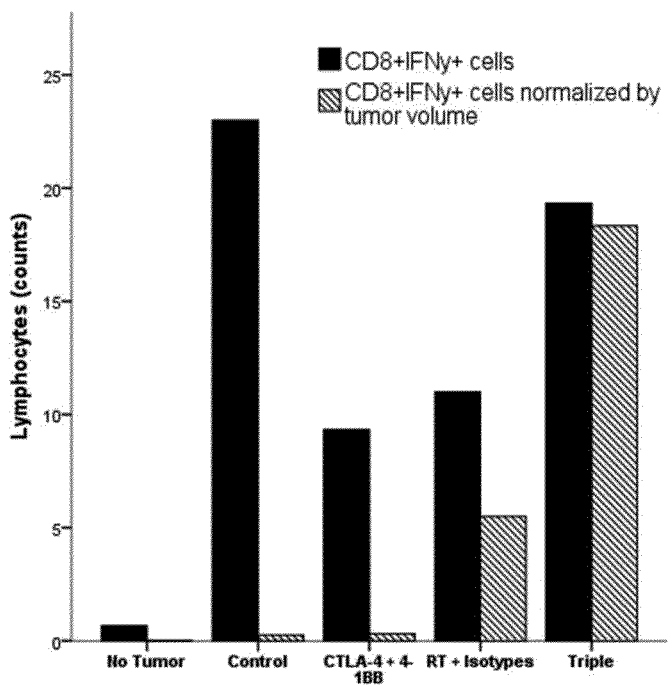

FIGS. 10A and 10B are graphs depicting the numbers of CD4+ and CD8+ cells producing IFN-y. There is no difference in the absolute counts of TILs through the treatment groups. However, harvested brain from the radiation plus anti-4-1BB and anti-CTLA-4 group had smaller tumors.

Figure 11:
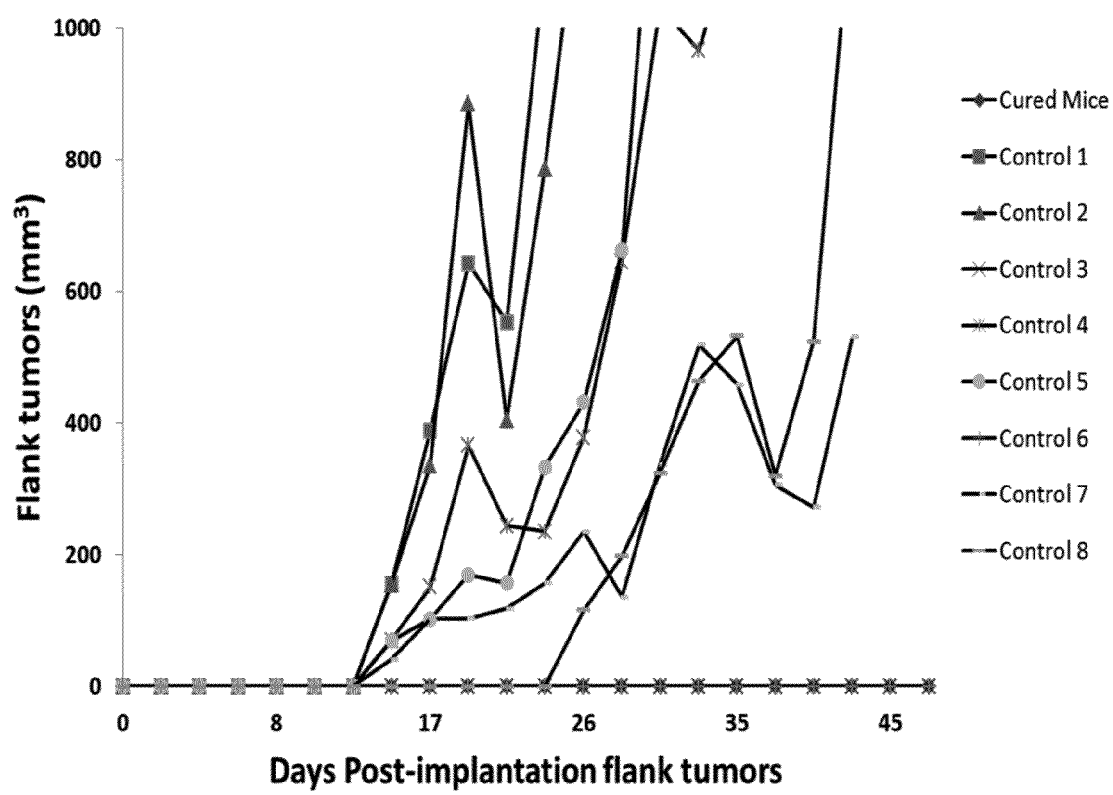

FIG. 11 is a graph showing protective memory response. The tumor size was graphed after tumor re-challenge. Flank tumor growth was monitored for an additional 50 days. All naïve animals had palpable tumors by day 17, whereas the long-term survivors had no sign of tumor growth by day 50.

Figure 12:
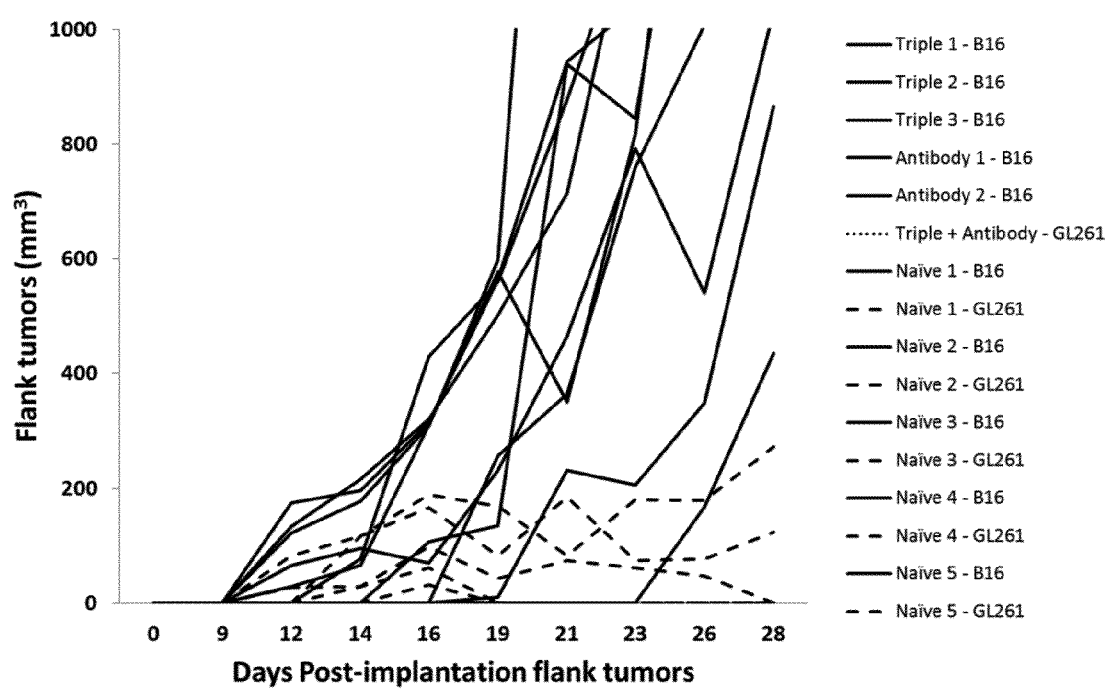

FIG. 12 is a graph depicting the specificity of the memory response. Cured and naïve mice were injected subcutaneous with $10^6$ GL261-LUC cells in the left flanks and $10^5$ B16-LUC cells in the right flanks. Naïve animals had palpable tumors on both flanks; growth of GL261 and B16 tumors. However, cured animals grew only tumors on the right flanks and no tumors on the left flanks; growth of B16 tumors only.

DETAILED DESCRIPTION OF THE INVENTION

The presently disclosed subject matter now will be described more fully hereinafter with reference to the accompanying figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

In accordance with embodiments of the present invention, the disclosed subject matter provides an approach whereby the immune system is activated and then maintained to promote an effective antitumor response in a subject.

In one or more embodiments, the present invention provides methods which use focused radiation as an initiator for immunotherapy against a tumor in a subject.

In accordance with one or more embodiments, the present invention provides methods of treatment of tumors using focused radiation on a subject to initiate an immune response in the subject, followed by administration of an immunotherapeutic agent, such as a PD-1 antibody, to bypass immune checkpoints and sustain the immune response in the subject.

Therefore, in accordance with an embodiment, the present invention provides methods for treating a tumor in a subject in need of treatment thereof, the method comprising administering to the subject a therapeutically effective dose of focused radiation to treat the tumor in combination with at least one immunotherapeutic agent comprising an immune checkpoint inhibitor.

As used herein, the term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

It will be understood by those of ordinary skill in the art, that the term "immune checkpoints" means a group of molecules on the cell surface of CD4 and CD8 T cells. These molecules effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells immunotherapeutic agents which can act as immune checkpoint inhibitors useful in the methods of the present invention, include, but are not limited to, anti-B7-H4; anti-PD1 or anti-B7-H1; anti-CTLA-4 (ipilimumab) and anti-LAG3.

More particularly, as also described in more detail herein below, ipilimumab (anti CTLA-4) is a fully human, antagonistic monoclonal antibody that binds to CTLA-4. CTLA-4 is a cell-surface protein expressed on certain CD4 and CD8 T cells; when engaged by its ligands (B7-1 and B7-2) on APCs, T-cell activation and effector function are inhibited. When an antibody to CTLA-4 is administered, the CTLA-4 receptor can no longer bind to these ligands, and T-cell responses are unrestrained. Ipilimumab has been evaluated in a number of clinical trials in melanoma, renal cell cancer, and more recently in prostate cancer.

In accordance with another embodiment of the present invention, another immune checkpoint that could potentially be exploited for treating certain cancers is the inhibitory co-receptor known as programmed death 1 (PD-1 or CD279). Among the CD8 T cells that infiltrate the prostate gland in men with cancer, up to 87% express PD-1. Tumor-specific expression of the major ligand of PD-1, B7-H1, is associated with poor prognosis in kidney cancer, as well as in other cancers in humans. Conversely, in multiple systems blocking PD-1: B7-H1 interactions causes tumors to regress. MDX-1106 is a genetically engineered, fully human immunoglobulin G4 (IgG4) monoclonal antibody specific for human PD-1 that was recently evaluated in a phase 1, dose-escalation trial.

In accordance with alternative embodiments of the present invention, immunotherapeutic agents can include proteins and/or antibodies to proteins and biomolecules including, for example, B- and T-lymphocyte attenuator protein (BTLA), Tim3, CD160, KIR antagonist antibodies, 4-1BB, OX40, CD27 and CD4.

Without wishing to be bound to any one particular theory, it is thought that focused radiation effectively disrupts the tumor microenvironment and causes presentation of tumor antigens to effectively act as a vaccine-like response. Current cancer vaccines are limited by the lack of tumor specific antigens. One advantage of focused radiation as compared to vaccines is that focused radiation precisely targets the tumor alone to cause spillage of multiple antigens that would be specific to the tumor.

In accordance with an embodiment, the present invention provides a method for activating and/or maintaining an immune system of a subject against a cancer to generate an anti-tumor response in a subject, the method comprising administering to the subject a therapeutically effective dose of focused radiation to activate and/or maintain the immune system against the cancer to promote an anti-tumor response in the subject.

In accordance with another embodiment, the present invention provides a method for inhibiting, reducing, or counteracting an immunosuppressive effect of a tumor in a subject, the method comprising administering to the subject a therapeutically effective dose of focused radiation to inhibit or reduce the immunosuppressive effect of the tumor.

In accordance with a further embodiment, the present invention provides a method for initiating or increasing a presence of a cancer antigen in a tumor microenvironment in a subject, the method comprising administering to the subject a therapeutically effective dose of focused radiation to initiate or increase the presence of a cancer antigen in a tumor microenvironment in the subject.

As used herein the term "tumor microenvironment" includes the cells, including normal cells, molecules, and blood vessels that surround and feed a tumor cell. A tumor can change its microenvironment, and the microenvironment can affect how a tumor grows and spreads. More particularly, the tumor microenvironment is a complex system of many cells, which all can participate in tumor progression, including endothelial cells and their precursors, pericytes, smooth-muscle cells, fibroblasts of various phenotypes, myofibroblasts, neutrophils and other granulocytes (eosinophils and basophils), mast cells, T, B and natural killer lymphocytes, and antigen-presenting cells, such as macrophages and dendritic cells. The components of the microenvironment generally can be grouped into four categories: cancer cells, non-cancer cells, secreted soluble factors, and non-cellular solid material, including the extra-cellular matrix.

In accordance with an embodiment, the present invention provides a method for treating a tumor in a subject in need of treatment thereof, the method comprising administering to the subject a therapeutically effective dose of focused radiation to treat the tumor in combination with at least one immunotherapeutic agent.

As described in more detail herein below, the focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray).

In accordance with one or more embodiments, the present invention provides methods for administering a therapeutically effective amount of at least one immunotherapeutic agent in combination with the therapeutically effective dose of focused radiation. In particular embodiments, the immunotherapeutic agents are selected from the group consisting of monoclonal antibodies, immune effector cells, vaccines, including dendritic cell vaccines, and cytokines.

As described in further detail herein below, the monoclonal antibodies used in the inventive compositions and methods can be selected from the group consisting of anti-PD-1 antibody, alemtuzumab, bevacizumab, brentuximab vedotin, cetuximab, gemtuzumab ozogamicin, ibritumomab tiuxetan, ipilimumab (anti-CTLA-4), ofatumumab, panitumumab, rituximab, tositumomab, trastuzumab, anti-B7-H4, anti-B7-H1, anti-LAG3, BTLA, anti-Tim3, anti-B7-DC, anti-CD160, KIR antagonist antibodies, anti-4-1BB, anti-OX40, anti-CD27, and CD40 agonist antibodies.

In accordance with an embodiment, the present invention provides methods of treatment wherein focused radiation is used to complement an immune-based therapy of blocking the PD-1 receptor and allowing for a sustained immune response. As provided in more detail in the examples, the presently disclosed data demonstrates that combining SRS with PD-1 blockade is synergistic and more effective than each therapy alone in a mouse GBM model.

In accordance with a further embodiment, the present invention provides a pharmaceutical composition comprising at least one immunotherapeutic agent, wherein the composition includes a pharmaceutically and physiologically acceptable carrier, in an amount effective for use in a medicament, and most preferably for use as a medicament for inducing an immune response, or treating cancer, or inhibiting the growth of a tumor, or neoplasm in a subject who receives or will receive focused radiation treatment, when administered to the subject in an effective amount.

In accordance with still another embodiment, the present invention provides a use of at least one immunotherapeutic agent, such as an immune checkpoint inhibitor, in the preparation of a pharmaceutical composition for the treatment of a clinical condition in an individual who receives or will receive focused radiation treatment.

In accordance with yet another embodiment, the present invention provides a neoadjuvant strategy or treatment regimen for treating cancer. It will be understood by those of ordinary skill in the art, that the term "neoadjuvant therapy" includes the administration of one or more therapeutic or immunotherapeutic agents in combination with focused radiation before, or in conjunction with, traditional chemotherapy/radiation treatment and adjuvant therapy. Neoadjuvant therapy aims to reduce the size or extent of the cancer before using radical treatment intervention, thus making procedures easier and more likely to succeed, and reducing the consequences of a more extensive treatment technique that would be required if the tumor wasn't reduced in size or extent.

As used herein, the term "therapeutic agent(s)" encompasses drugs and other active agents, such as chemotherapeutic agents, immunotherapeutic agents, such as, for example, immune checkpoint inhibitors.

FIG. 7 depicts a comparison of a standard prior art tumor treatment regimen (left) and a representative neoadjuvant treatment regimen of the present invention (right). In this representative, non-limiting strategy, a patient is administered focused radiation in combination with a first dose of an antibody days after receiving a result from a biopsy. After a period of time later, for example, a week later, the patient can undergo surgery. Following surgery, for example, two weeks after surgery, the patient is administered focused radiation in combination with a second dose of an antibody. After another period of time, for example two weeks later, the patient is administered focused radiation in combination with a third dose of an antibody. One of ordinary skill in the art would recognize upon review of the presently disclosed subject matter that the treatment regimen presented in FIG. 7 can be adjusted or modified to meet the therapeutic needs of an individual patient. For example, any of the steps disclosed in FIG. 7 can be repeated in series, or individually, to meet such needs.

In accordance with another embodiment, the present inventive methods further comprise administering to the subject additional chemotherapy, immunotherapy and or radiation treatment. In other embodiments, the method further comprises administering to the subject, adjuvant therapy.

In accordance with another embodiment, the present inventive methods further comprise administering at least one adjuvant to the subject in combination with the at least one immunotherapeutic agent and/or immune checkpoint inhibitor. In particular embodiments, the adjuvant is selected from the group consisting of a cytokine, an interleukin, an interferon, a granulocyte-macrophage colony-stimulating factor (GM-CSF), Bacille Clamette-Guérin (BCG), a keyhole limpet memocyanin (KLH), incomplete Freund's adjuvant (IFA), QS-21, DETOX, and dinitrophenyl.

It will be understood that the inventive methods can be used to treat many tumors, both benign and malignant. In one or more embodiments, the invention provides methods and compositions for treating cancers, including, for example, cancers which exist as solid tumors in a subject. One of ordinary skill in the art, upon review of the presently disclosed subject matter, would understand that other tumors, including solid tumors, lesions, and conditions can be treated by the presently disclosed methods including, but not limited to, cancers involving the brain; cancers involving the spine; lung cancers; pancreatic cancers; prostate cancers; liver cancers, kidney cancers; breast cancers, melanoma, metastatic orbital tumors, orbital lymphomas, and orbital inflammations; benign brain tumors, such as acoustic neuromas, meningiomas, pituitary adenomas, craniopharngiomal hemangioblastoma, schwannomas; malformations of blood vessels within the brain, such as arteriovenous malformations (AVMs) and trigieminal neuralgia.

In accordance with an embodiment of the present invention, the tumor being treated is a brain tumor. In more particular embodiments, the brain tumor is selected from the group consisting of a glioblastoma, an astrocytoma, an oligodendroglioma, an ependymoma, and a metastatic brain tumor.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed treatment regimens can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject."

Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an agent, e.g., a dose of radiation and/or an immunotherapeutic agent, refers to the amount necessary to elicit the desired biological response. As will be appreciated by those of ordinary skill in this art, the effective amount of an agent may vary depending on such factors as the desired biological endpoint, the agent to be delivered, the makeup of the agent, the target tissue, and the like.

The term "combination" is used in its broadest sense and means that a subject is administered at least two agents, e.g., a dose of radiation and at least one immunotherapeutic agent, e.g., monoclonal antibodies, immune effector cells, vaccines, including dendritic cell vaccines, and cytokines, as described herein or as otherwise known in the art.

In accordance with one or more embodiments of the methods of the present invention, the timing of administration of a dose of radiation and the at least one immunotherapeutic agent can be varied so long as the beneficial effects of the combination of these agents are achieved. Accordingly, the phrase "in combination with" refers to the administration of a dose of radiation and at least one immunotherapeutic agent either simultaneously, sequentially, or a combination thereof. Therefore, a subject administered a combination of a dose of radiation and at least one immunotherapeutic agent can receive a dose of radiation and at least one immunotherapeutic agent at the same time (i.e., simultaneously) or at different times (i.e., sequentially, in either order, on the same day or on different days), so long as the effect of the combination of both agents is achieved in the subject.

It will be understood by those of ordinary skill, that when administered sequentially, the immunotherapeutic agents can be administered within 1, 5, 10, 30, 60, 120, 180, 240 minutes or longer of one another. In other embodiments, agents administered sequentially, can be administered within 1, 5, 10, 15, 20 or more days of one another. When more than one therapeutic agent is administered in combination with a dose of radiation, and the agents are administered either sequentially or simultaneously, they can be administered to the subject as separate pharmaceutical compositions, each comprising either one therapeutic agent and at least one immunotherapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent(s) was administered as a single agent. The effects of multiple agents may, but need not be, additive or synergistic. The agents may be administered multiple times.

As used herein, the terms "synergy," "synergistic," "synergistically" and derivations thereof, such as in a "synergistic effect" or a "synergistic combination" or a "synergistic composition" refer to circumstances under which the biological activity of a combination of a dose of radiation and at least one additional therapeutic agent is greater than the sum of the biological activities of the respective agents when administered individually.

Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In summary, the presently disclosed methods provide a novel treatment regimen for disrupting the tumor microenvironment. Further, the presently disclosed methods have implications beyond brain cancers, because the technology necessary to deliver stereotactic radiation to cancers in other parts of the body currently exists. Accordingly, the presently disclosed subject matter can improve the understanding of the complex mechanisms of immune cell suppression by tumor cells and introduce a new paradigm for the treatment of GBMs.

Furthermore, the methods of the present invention can promote a sustained antitumor response when animals are subsequently re-challenged with tumor cells after receiving an initial treatment. In accordance with an embodiment, the present invention provides methods which effectively generate an immune response in a subject and overcome the immunosuppressive effects of the tumor in a subject. It will be understood by those of ordinary skill in the art, that the combination of focused radiation with at least one immunotherapeutic agent, such as an antibody, as provided by the present invention, improves survival compared to each therapy alone and, lead to a durable cure.

Focused radiation methods suitable for use with the presently disclosed methods include, but are not limited to, stereotactic radiosurgery, fractionated stereotactic radiosurgery, and intensity-modulated radiation therapy (IMRT).

It will be understood by those of ordinary skill in the art, stereotactic radiosurgery involves the precise delivery of radiation to a tumorous tissue, for example, a brain tumor, while avoiding the surrounding non-tumorous, normal tissue. Because stereotactic radiosurgery is so precise, it allows a higher dose of radiation to be given with more sparing of normal tissue than can be achieved with conventional radiotherapy techniques. To achieve this precision, specific procedures for identifying the position of the tumorous tissue are used. For example, information from magnetic resonance imaging (MRI) and/or computed tomography (CT) scans can be transferred directly to a treatment-planning computer system to create a three-dimensional (3-D) model of the tumor and surrounding normal tissue. The 3-D image allows the position of the abnormality to be treated to be identified and targeted. A complex radiation delivery planning system is used to target a high dose of radiation at the tumor while greatly limiting the dose to nearby normal tissue. Special devices are used to keep the subject still so that the radiation will be aimed with great accuracy at the targeted tumor.

Various types of radiosurgery used in the inventive methods can be used to treat many different tumors, e.g., a brain tumor, both benign and malignant. The malignant tumors treated most often by radiosurgery include, but are not limited to, brain metastases or tumors that have spread to the brain. Malignant gliomas have been treated with radiosurgery at the time of recurrence. Further, many benign tumors can be treated with radiosurgery. Such benign tumors include, but are not limited to, vestibular schwannomas (acoustic neuromas), meningiomas, and pituitary adenomas.

Because of noninvasive fixation devices, stereotactic radiation need not be delivered in a single treatment. The treatment plan can be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment.

In an embodiment, the dosage of radiation applied using stereotactic radiosurgery can vary. In some embodiments, the dosage can range from 1 Gy to about 30 Gy, and can encompass intermediate ranges including, for example, from 1 to 5, 10, 15, 20, 25, up to 30 Gy in dose.

The main advantage of fractionation is that it allows higher doses to be delivered to tumorous tissue because of an increased tolerance of the surrounding normal tissue to these smaller fractionated doses. Accordingly, while single-dose stereotactic radiation takes advantage of the pattern of radiation given, fractionated stereotactic radiation takes advantage of not only the pattern of radiation, but also of the differing radiosensitivities of normal and surrounding tumorous tissues. Another advantage of fractionated stereotactic radiation is so-called "iterative" treatment, in which the shape and intensity of the treatment plan can be modified during the course of therapy.

Fractionated stereotactic radiosurgery can result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation can kill more normal tissue than several smaller doses of radiation can. Accordingly, multiple smaller doses of radiation can kill more tumor cells while sparing normal tissue.

In an embodiment, the dosage of radiation applied using fractionated stereotactic radiation can vary. In some embodiments, the dosage can range from 1 Gy to about 50 Gy, and can encompass intermediate ranges including, for example, from 1 to 5, 10, 15, 20, 25, 30, 40, up to 50 Gy in hypofractionated doses.

For vestibular schwannomas, fractionated stereotactic radiosurgery (FSR) can often spare the facial motor and sensory nerves. FSR is particularly useful for treating meningiomas that can be difficult to remove by conventional surgery because of location near the skull base or cavernous sinus or for meningiomas that are recurrent after surgery and regular radiation. For example, for pituitary adenomas, FSR can spare the optic nerve and chiasm, as well as the hypothalamus, thus sparing the releasing hormones that drive the normal pituitary. Other tumors that benefit from FSR include, but are not limited to, hemangioblastomas, chordomas, low grade (pilocytic) astrocytomas, hemangiopericytomas, and others.

Another advance in stereotactic radiation treatment is the development of three-dimensional images of the tumor and surrounding tissues. Sophisticated software can take small, e.g., 2-mm, cuts from either CT or MRI scans and convert them into three-dimensional images. Three-dimensional treatment planning delivers a high-precision dose to the tumor, while sparing normal tissue, and can achieve more efficacious results than can be achieved with two-dimensional planning. Accordingly, FSR treatments using fusion of MRI and CT images can achieve high sensitivity and precision of target delineation.

It will be understood by those of ordinary skill in the art that stereotactic radiosurgery can be characterized by the source of radiation used, including particle beam (proton), cobalt-60 (photon-Gamma Knife®), and linear accelerator (x-ray). A linear accelerator produces high-energy X-ray radiation and is capable of delivering precise and accurate doses of radiation required for radiosurgery. Radiosurgery using a linear accelerator is typically carried out in multi-session, smaller dose treatments so that healthy surrounding tissue is not damaged from too high a dose of radiation. Radiosurgery using linear accelerator technology also is able to target larger brain and body cancers with less damage to healthy tissues. The most common uses of linear accelerator stereotactic radiosurgery are for the treatment of metastatic cancer, some benign tumors and some arterio-venous malformations. Linear accelerator based machines are not dedicated to treatments only within the brain and can be used throughout the body, as well as the head and neck.

As used with the inventive methods and compositions provided herein, a "gamma knife" uses multiple, e.g., 192 or 201, highly-focused x-ray beams to make up the "knife" that cuts through diseased tissue. The gamma knife uses precisely targeted beams of radiation that converge on a single point to painlessly "cut" through brain tumors, blood vessel malformations, and other brain abnormalities. A gamma knife makes it possible to reach the deepest recesses of the brain and correct disorders not treatable with conventional surgery.

In accordance with the inventive methods and compositions, use of proton beam radiation offers certain theoretical advantages over other modalities of stereotactic radiosurgery (e.g., Gamma Knife® and linear accelerators), because it makes use of the quantum wave properties of protons to reduce doses of radiation to surrounding tissue beyond the target tissue. In practice, the proton beam radiation offers advantages for treating unusually shaped brain tumors and arteriovenous malformations. The homogeneous doses of radiation delivered by a proton beam source also make fractionated therapy possible. Proton beam radiosurgery also has the ability to treat tumors outside of the cranial cavity. These properties make proton beam radiosurgery efficacious for post-resection therapy for many chordomas and certain chondrosarchomas of the spine and skull base, as well as a mode of therapy for many other types of tumors.

In accordance with another embodiment of the inventive methods and compositions, intensity-modulated radiation therapy (IMRT) can be used. IMRT is an advanced mode of high-precision three-dimensional conformal radiation therapy (3DCRT), which uses computer-controlled linear accelerators to deliver precise radiation doses to a malignant tumor or specific areas within the tumor. In 3DCRT, the profile of each radiation beam is shaped to fit the profile of the target from a beam's eye view (BEV) using a multileaf collimator (MLC), thereby producing a number of beams. More particularly, IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel.

Treatment with IMRT is planned by using 3-D computed tomography (CT) or magnetic resonance (MRI) images of the patient in conjunction with computerized dose calculations to determine the dose intensity pattern that will best conform to the tumor shape. Typically, combinations of multiple intensity-modulated fields coming from different beam directions produce a custom tailored radiation dose that maximizes tumor dose while also minimizing the dose to adjacent normal tissues. Because the ratio of normal tissue dose to tumor dose is reduced to a minimum with the IMRT approach, higher and more effective radiation doses can safely be delivered to tumors with fewer side effects compared with conventional radiotherapy techniques. IMRT typically is used to treat cancers of the prostate, head and neck, and central nervous system. IMRT also has been used to treat breast, thyroid, lung, as well as in gastrointestinal, gynecologic malignancies and certain types of sarcomas.

In accordance with one or more embodiments, the present invention provides compositions and methods of treatment which include immunotherapies. As used herein, the term "immunotherapy" includes the treatment of a disease or condition by inducing, enhancing, or suppressing an immune response in the subject. It is understood by those of ordinary skill in the art that immunotherapies that are designed to elicit or amplify an immune response are classified as activation immunotherapies, while immunotherapies that reduce or suppress an immune response are classified as suppression immunotherapies. The active agent in immunotherapy is referred to as an immunotherapeutic agent. Representative agents useful in the methods of the present invention include, but are not limited to, interleukins, such as IL-2, IL-7, and IL-12; cytokines, such as interferons, G-CSF, and imiquimod; chemokines; and other agents, such as cytosine phosphate-guanosine, oligodeoxynucleotides, and glucans. Representative immunotherapies suitable for use with the presently disclosed methods include, but are not limited to, a cytokine-based therapy, a passive immune-based strategy, including antibody therapy and adoptive therapy, and an active therapy, including a vaccine, such as a dendritic cell based vaccine.

In accordance with an embodiment, the immunotherapies used in the compositions and methods of the present invention include the use of immune checkpoint inhibitors.

Immunotherapy, as used in the inventive methods and compositions, is generally understood to work in two ways: active immunotherapies stimulate one's own immune system to fight the disease, whereas passive immunotherapies use immune system components (such as antibodies) made in the lab. Alternatively, some immunotherapies work by targeting a certain type of cell. Most immunotherapies target one kind of cell or antigen (specific immunotherapies), but there are some immunotherapies that stimulate the immune system in general (non-specific immunotherapies). In certain cases, non-specific immunotherapies are used with other treatments (as an adjuvant) to increase the attack on the cancer.

More particularly, the immunotherapy used in the compositions and methods of the present invention is the use of a subject's immune system to reject and to destroy cancerous tumors. The main premise behind cancer immunotherapy is to stimulate a subject's immune system to attack malignant tumor cells. Cancer immunotherapy can be carried out either through immunization of the subject, e.g., by administering a cancer vaccine, such as sipuleucel-T for prostate cancer, in which the subject's immune system recognizes tumor cells to be destroyed, or through the administration of therapeutic antibodies, in which the subject's immune system is recruited by the therapeutic antibodies to destroy the tumor cells.

It is understood by those of ordinary skill in the art that in certain cases, cell-based immunotherapies have proven to be effective for some cancers. For example, immune effector cells, such as lymphocytes, macrophages, dendritic cells, natural killer cells, lymphokine activated killer cells, cytotoxic T lymphocytes, and the like, can defend against cancer by targeting abnormal antigens expressed on the surface of a tumor due to mutation. Such cells are either activated in vivo by administering certain cytokines, such as interleukins, or they are isolated, enriched and transfused to the subject. The injected immune cells are highly cytotoxic to the cancer cells.

Another type of cancer immunotherapy suitable for use with the inventive methods involves monoclonal antibodies. Antibodies play a central role in the recognition of foreign antigens and the stimulation of an immune response to a foreign antigen, e.g., an antigen on the surface of a cancer cell. The advance of monoclonal antibody technology has made it possible to raise antibodies against specific antigens, including antigens presented on the surface of a tumor. A number of therapeutic monoclonal antibodies have been approved for use in humans, and can be used in the present invention, including, but not limited to, alemtuzumab, bevacizumab, brentuximab vedotin, cetuximab, gemtuzumab ozogamicin, ibritumomab tiuxetan, ofatumumab, panitumumab, rituximab, tositumomab, and trastuzumab.

Two types of monoclonal antibodies typically are used in cancer treatments and in the inventive methods: naked monoclonal antibodies without any drug or radioactive material attached to them; and conjugated monoclonal antibodies, which are bound to a chemotherapy drug, radioactive particle, or a toxin (a substance that poisons cells). Naked MAbs are the most commonly used MAbs at this time for cancer treatment. Although they work by attaching themselves to specific antigens, naked MAbs can be helpful in different ways, including as markers for destruction in which they attach to cancer cells to act as a marker for the body's immune system to destroy them. Antibodies in this group include: rituximab, ofatumumab, alemtuzumab.

Some naked MAbs don't actually interact with a subject's own immune system. Their effects come from their ability to attach to specific antigens of cancer cells or other cells that help cancer cells grow, and stop them from working, i.e., as activation blockers. These MAbs are also referred to as targeted therapies. Examples of U.S. FDA-approved MAbs of this type which can also be included in the methods of the present invention include: trastuzumab, cetuximab, panitumumab, and bevacizumab.

Further, conjugated MAbs are monoclonal antibodies that are attached to drugs, toxins, or radioactive substances. Such MAbs are used as homing devices to take these substances directly to the cancer cells. The MAb circulates in the body until it can find and attach to the target antigen, where it then delivers the toxic substance where it is needed most. This property lessens the damage to normal cells in other parts of the body. Conjugated antibodies can be divided into the following groups, depending on what they are linked to: MAbs with radioactive particles attached are referred to as radiolabeled, and therapy with this type of antibody is known as radioimmunotherapy (RIT); MAbs with chemotherapy drugs attached are often referred to as chemolabeled; and MAbs attached to toxins are called immunotoxins.

Currently, there are two radiolabeled antibodies are currently approved to treat cancer. Ibritumomab tiuxetan delivers radioactivity directly to cancerous B lymphocytes and is used to treat B-cell non-Hodgkin lymphoma that has not responded to standard treatment. Tositumomab is used to treat certain types of non-Hodgkin lymphoma that no longer respond to rituximab or standard chemotherapy.

The only chemolabeled antibody that is currently approved to treat cancer is brentuximab vedotin, which is made up of an antibody that targets the CD30 antigen attached to a chemotherapeutic agent called monomethyl auristatin E. Brentuximab vedotin is used to treat Hodgkin lymphoma and anaplastic large cell lymphoma that is no longer responding to other treatments.

Immunotoxins can be made by attaching MAbs to bacterial toxins, such as diphtheria toxin (DT) or pseudomonal exotoxin (PE40), or to plant toxins such as ricin A or saporin. No immunotoxins are currently approved for treating cancer at this time. Gemtuzumab ozogamicin was approved for some time to treat some subjects afflicted with acute myelogenous leukemia. It contains a toxin called calicheamicin, attached to an antibody against the CD33 antigen, which is present on most leukemia cells. Further studies of this drug did not show that it helped patients live longer and the approval was withdrawn. It is no longer available for use outside of a clinical trial.

Another immunotoxin, BL22, showed promising results in early studies against some forms of chronic leukemia, even in patients who no longer responded to chemotherapy. In early clinical trials, about 2 of 3 patients had complete responses to the treatment (no evidence of cancer) that lasted up to 2 years. A newer, improved version of this immunotoxin, known as HA22 (CAT-8015), is now being studied. Clinical trials of other immunotoxins also are currently being done in people with certain leukemias, lymphomas, brain tumors, and other cancers.

Particular monoclonal antibodies and their uses in treating particular forms of cancer are provided immediately hereinbelow:

Alemtuzumab is an anti-CD52 humanized IgG1 monoclonal antibody indicated for the treatment of chronic lymphocytic leukemia (CLL). The function of CD52 is unknown, but it is found on >95% of peripheral blood lymphocytes and monocytes. Upon binding to CD52, alemtuzumab initiates its cytotoxic effect by complement fixation and antibody-dependent cell-mediated cytotoxicity mechanisms. Alemtuzumab therapy is also indicated for T-prolymphocytic leukemia (TPPL).

Bevacizumab is a humanized IgG1 monoclonal antibody which binds to and sterically interferes with the vascular endothelial growth factor-A (VEGF-A), thereby preventing receptor activation. The VEGF protein is normally made by tumor cells to attract new blood vessels to feed their growth. A marked increase in VEGF expression is thought to play a role in tumor angiogenesis. Bevacizumab is indicated for colorectal cancer; but has been applied to numerous other cancers including non-small cell lung cancer, breast cancer, glioblastoma, kidney cancer, and renal cell carcinoma.

Brentuximab vedotin is approved for use against Hodgkin lymphoma and anaplastic large cell lymphoma (a type of non-Hodgkin lymphoma).

Cetuximab is a chimeric IgG1 monoclonal antibody that targets the extracellular domain of the epidermal growth factor receptor (EGFR). It functions by competitively inhibiting ligand binding, thereby preventing EGFR activation. Cetuximab is indicated for the treatment of colorectal cancer and head and neck cancer. Studies also have been carried out on numerous other malignancies, including non-small cell lung cancer. Other anti-EGFR monoclonal antibodies in development include ABX-EGF, hR3, and EMD 72000.

Denosumab binds to a protein called Rank ligand. This protein is made by cancer cells when they attack bone. Accordingly, denosumab helps to stop cancer cells that have spread from destroying bone tissue. Denosumab is approved for use against cancer that has spread to bone.

Gemtuzumab ozogamicin is an "immuno-conjugate" of an anti-CD33 antibody chemically linked to calicheamicin, a cytotoxic agent. Gemtuzumab ozogamicin is indicated for the treatment of acute myeloid leukemia (AML), although at this point is only approved for use in clinical trials. The patient group most likely to benefit from gemtuzumab is young adults, and trials have reported high complete responses (e.g., 85%), when combined with intensive chemotherapy.

Ibritumomab tiuxetan is an anti-CD20 antibody and can be used as a radioimmunotherapy to treat some forms of B-cell non-Hodgkin lymphoma, e.g., follicular lymphoma, in combination with yttrium-90 or indium-111. More particularly, ibritumomab tiuxetan is a murine antibody chemically linked to a chelating agent that binds yttrium-90 or indium-111.

Ipilimumab does not bind to cancer cells. Instead it binds to CTLA-4, an antigen that is found on both regulatory T cells (Treg cells) and cytotoxic T cells. Ipilimumab works in two ways. It lowers the numbers of Treg cells, which in essence releases the immune system, allowing it to fight the cancer. It also binds to cytotoxic T cells, allowing them to act to kill cancer cells. Ipilimumab is approved for use in treating melanoma.

Tositumomab/Iodine is another form of radioimmunotherapy. Tositumomab is a murine IgG2a anti-CD20 antibody, which can be covalently bound to Iodine ($^{131}$I). Clinical trials have established the efficacy of a sequential application of tositumomab and iodine ($^{131}$I) tositumomab in patients with relapsed follicular lymphoma.

Ofatumumab is another antibody against the CD20 antigen. It is used mainly to treat chronic lymphocytic leukemia when other treatments are no longer effective.

Panitumumab is a fully human monoclonal antibody specific to the epidermal growth factor receptor (also known as EGF receptor, EGFR, ErbB-1 and HER1 in humans). Panitumumab is approved by the U.S. FDA for the treatment of EGFR-expressing metastatic colorectal cancer with disease progression despite prior treatment.

Rituximab is a chimeric monoclonal antibody specific for CD20, which is widely expressed on B-cells. Although the function of CD20 is relatively unknown it has been suggested that CD20 could play a role in calcium influx across plasma membrane, maintaining intracellular calcium concentration and allowing for the activation of B cells. The exact mode of action of rituximab also is unclear, but it has been found to have a general regulatory effect on the cell cycle and on immune-receptor expression and is thought to label cells so that the immune system can attack them. Experiments involving primates showed that treatment with anti-CD20 reduced peripheral B-cells by 98%, and peripheral lymph node and bone marrow B-cells by up to 95%. Rituximab is approved for use in B-cell non-Hodgkin lymphoma and chronic lymphocytic leukemia (CLL).

Trastuzumab is a monoclonal IgG1 humanized antibody specific for the epidermal growth factor receptor 2 protein (HER2). It received FDA-approval in 1998, and is clinically used for the treatment of breast cancer. The use of trastuzumab generally is restricted to patients whose tumors overexpress HER-2. Trastuzumab also is approved for use in stomach cancer having a large amount of HER2/new protein.

In accordance with an embodiment, the present invention provides a method for treatment of tumors wherein the treatment comprises use of adoptive cell transfer in conjunction with radiotherapy. Adoptive cell transfer uses T-cell-based cytotoxic responses to attack cancer cells. In accordance with the inventive methods, T-cells having a natural or genetically engineered reactivity to a subject's cancer are generated in vitro and then transferred back to the subject. This process can be achieved by taking T-cells associated with a particular tumor of the subject that are trained to attack the cancerous cells. Such T-cells are referred to as tumor-infiltrating lymphocytes (TIL) and are encourage to multiply in vitro using high concentrations of IL-2, anti-CD3, and allo-reactive feeder cells. The T-cells can be transferred back into the subject along with exogenous administration of IL-2 to further boost their anti-cancer activity.

Cancer vaccines have been studied for several decades, but advances in this field have been slower than for other forms of immunotherapy and they are still mostly experimental treatments at this time. Vaccines, in general, use weakened or killed viruses, bacteria, or other germs to trigger an immune response in the body to defend against a foreign antigen. Cancer vaccines are designed to work the same way. For example, new vaccines against the human papilloma virus (HPV) help prevent cervical, vaginal, vulvar, and anal cancer. Vaccines against hepatitis B virus (HBV) may lower some subject's risk of getting liver cancer. But these vaccines don't target cancer cells; they target the viruses that can cause these cancers.

True cancer vaccines are different from the vaccines that work against viruses. Instead of preventing disease, they are meant to promote the immune system to attack the cancer itself. A true cancer vaccine has cancer cells, parts of cells, or pure antigens. The vaccine increases the immune response against cancer cells that are already in the body and can be combined with other substances or cells called adjuvants that help boost the immune response.

Cancer vaccines are characterized as active immunotherapies because they are meant to trigger a subject's own immune system to respond. Further, cancer vaccines are specific because they should only affect cancer cells. Such vaccines don't just boost the immune system in general; they cause the immune system to attack cancer cells with one or more specific antigens. At this time, only one true cancer vaccine has been approved by the FDA. Sipuleucel-T (Provenge®) is used to treat advanced prostate cancer. In this vaccine, white blood cells (cells of the immune system) are removed from the patient's blood and exposed to a protein from prostate cancer cells called prostatic acid phosphatase (PAP). These exposed cells are then given back to the patient by infusion into a vein (IV). Once in the body, the cells make other immune system cells attack the patient's prostate cancer.

Other types of cancer vaccines are currently being studied including, but not limited to, tumor cell vaccines, including autologous and allogeneic tumor cell vaccines; antigen vaccines, which boost the immune system by using only one or a few antigens, e.g., proteins or peptides; dendritic cell vaccine, which include special antigen-presenting cells (APCs) that help the immune system recognize cancer cells by breaking down cancer cells into smaller pieces (including antigens), then present these antigens to T cells making it easier for the immune system cells to recognize and attack them; anti-idiotype vaccines, which show promise as a B-cell lymphoma; DNA vaccines, and vector-based vaccines, which use special delivery systems (called vectors) to make them more effective and can include, for example, vector-based antigen vaccines and vector-based DNA vaccines.

Types of cancers for which tumor cell vaccines are being studied include, but are not limited to, melanoma, kidney cancer, ovarian cancer, breast cancer, colorectal cancer, lung cancer, prostate cancer, non-Hodgkin lymphoma, and leukemia. Antigen vaccines are being studied to be used against these cancers, among others: breast cancer, prostate cancer, colorectal cancer, ovarian cancer, melanoma, kidney cancer, pancreatic cancer, and multiple myeloma. The dendritic cell vaccine approach is being studied for use in subjects with these and other cancers: prostate cancer, melanoma, kidney cancer, colorectal cancer, lung cancer, breast cancer, leukemia, and non-Hodgkin lymphoma. Sipuleucel-T (Provenge), which is approved to treat advanced prostate cancer, is an example of a dendritic cell vaccine. DNA vaccines are now being studied in clinical trials for use against the following cancers, among others: melanoma, leukemia, prostate cancer, and head and neck cancers.

Whereas vaccines are designed to get the body's immune system to react to specific antigens, other active, specific immunotherapies boost specific parts of the immune system. Such immunotherapies include, but are not limited to, lymphokine-activated killer cell therapy; tumor-infiltrating lymphocyte vaccine with interleukin-2; and suppressing regulatory T cells.

Non-specific immunotherapies do not target a certain cell or antigen. Instead, they stimulate the immune system in a very general way, which can result in more activity against cancer cells. Some non-specific immunotherapies can be given as treatments, whereas others can be used as adjuvants (along with a main treatment) to boost an immune system function to improve the efficacy of another therapy. Some immunotherapies are used independently against some cancers and as adjuvants against others. Such non-specific immunotherapies include, but are not limited to, cytokines, interleukins, interferons, and granulocyte-macrophage colony-stimulating factor (GM-CSF).

Cytokines are chemicals made by immune system cells and have a crucial role in regulating the growth and activity of other immune system cells and blood cells. Some cytokines can be used to lessen the side effects of other treatment regimens, such as chemotherapy. Man-made cytokines can help bone marrow make more white blood cells, red blood cells, or platelets. While this function is important in cancer treatment, it isn't truly immunotherapy. Man-made cytokines also can be administered in combination with, for example, a tumor vaccine as an adjuvant, or given alone to boost the immune system.

Interleukins are a group of cytokines that act as chemical signals between white blood cells. Interleukin-2 (IL-2) was approved to treat advanced kidney cancer and also has been approved to treat subjects with metastatic melanoma. IL-2 can be used as a single drug treatment for these cancers or it can be combined with other forms of immunotherapy, such as vaccines. IL-2 helps immune system cells grow and divide more quickly.

Administering IL-2 in combination with chemotherapy or with one or more other cytokines, such as interferon-alfa, can make these treatments more effective against some cancers, but the side effects of the combined treatment also can be increased. Other interleukins, such as IL-7, IL-12, and IL-21, also are being studied for use against cancer as adjuvants and as stand-alone agents.

Interferons are a family of cytokines that help the body resist viral infections and cancers and include IFN-alpha, IFN-beta, and IFN-gamma IFN-alpha is used to treat cancer and is thought to act by one or more of the following mechanisms: directly slowing the growth of cancer cells; slowing down angiogenesis; causing cancer cells to produce more antigens, making them easier for the immune system to recognize and destroy; and boosting the cancer cell-killing ability of natural killer (NK) cells and of other immune system cells that attack cancer with help from antibodies. IFN-alpha is approved to treat the following cancers: hairy cell leukemia, chronic myelogenous leukemia, follicular non-Hodgkin lymphoma, cutaneous T-cell lymphoma, kidney cancer, melanoma, and Kaposi sarcoma.

Granulocyte-macrophage colony-stimulating factor (GM-CSF) is a cytokine/growth factor that causes the bone marrow to make more of certain types of immune system cells and blood cells including monocytes, macrophages, and dendritic cells. GM-CSF also boosts the production of other blood cells. A man-made version of GM-CSF (also known as sargramostim or Leukine®) is often used to boost white blood cell counts after chemotherapy. GM-CSF also is being evaluated against cancer as a non-specific immunotherapy and as an adjuvant given with other types of immunotherapies.

Adjuvants other than cytokines also are known to boost the activity of the immune system and are being evaluated as possible adjuvants, particularly for use with vaccine therapies. Such adjuvants include, but are not limited to, Bacille Calmette-Gueérin (BCG), a bacterium related to the one that causes tuberculosis, and is approved as a routine treatment for early stage bladder cancer. BCG also is being evaluated as an adjuvant to boost the immune system is subjects undergoing chemotherapy, radiation therapy, or other types of immunotherapy.

Keyhole limpet hemocyanin (KLH) is an adjuvant used to boost the effectiveness of cancer vaccine therapies. Incomplete Freund's adjuvant (IFA) stimulates the T-cell immune response to antigens and also is administered in combination with some experimental therapies to help stimulate the immune system and to increase the immune response to cancer vaccines. QS-21 is an immune stimulant made from a plant extract that increases the immune response to some cancer vaccines. DETOX is an adjuvant made from parts of the cell walls of bacteria and a kind of fat that also comes from bacteria. Since it was first made, other types, such as DETOX-B and DETOX-PC, have been created by using other methods and can be used with various immunotherapies to boost the immune system. Dinitrophenyl (DNP) is a small molecule that can attach to tumor antigens and boost immune response. It is used to modify tumor cells in certain cancer vaccines.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Figure 2A:
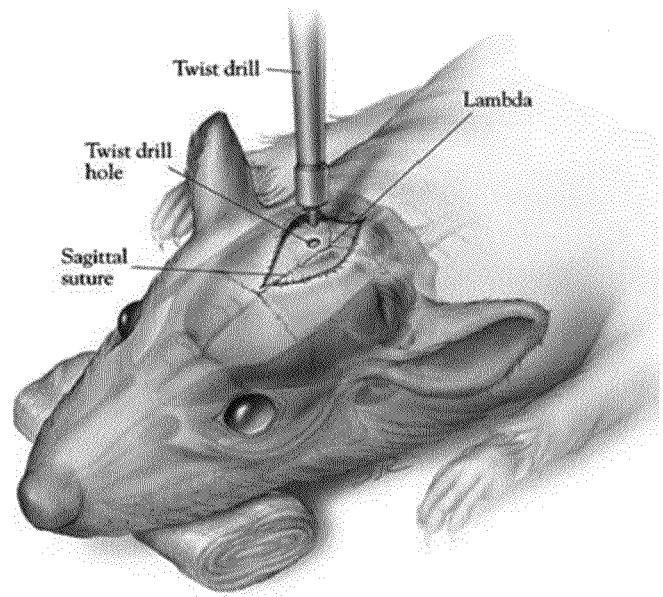
Figure 2B:
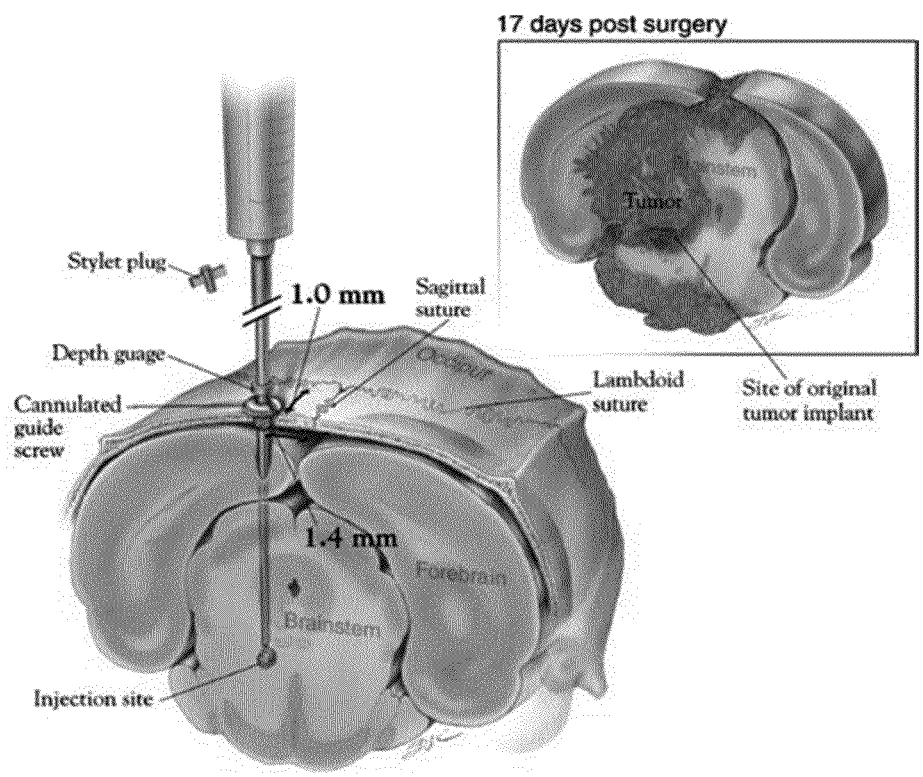
Figure 2C:
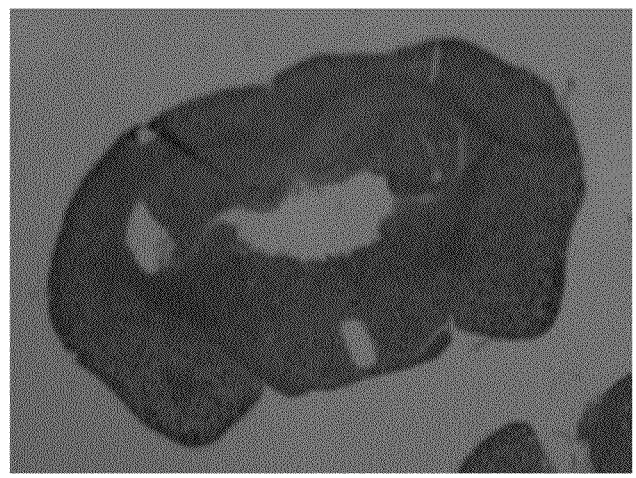
Figure 2D:

Tumor models. Intracranial tumor implantation of 130,000 GL261 cells transfected with luciferase was performed into C57/BL6 mice (FIGS. 2A and 2B). By day-10 post-implantation, histology showed a tumor visible on H&E stains, measuring approximately 1-2 mm in diameter (FIGS. 2C and 2D).

Example 2

Combining the immunotherapeutic agent anti-PD-1 antibody with radiation. On day-7 post-implantation, mice underwent bioluminescent imaging to assess tumor growth, and were stratified equally into one of four treatment arms: control, radiation, anti-PD-1 antibody, and radiation plus anti-PD-1 antibody. Anti-PD-1 antibody was given on days 10, 12, and 14 post-implantation, at dose 200 μg/mouse. Radiation therapy was given with a unique small animal research radiator platform (SARRP), which was developed by physicists at Johns Hopkins Medicine, and is a small-scale model of linear accelerators currently used to treat patients in clinics. The SARRP has a CT-scanner built into the radiator, which is able to perform CT scan to identify anatomy, and then deliver the radiation while the mouse is in the same position. Using the SARRP, the burr-hole from the intracranial implantation can be identified and a stereotactic 3-mm radiation beam can be targeted to 10 Gy centered on the tumor (FIGS. 3A-3C).

After the mice received the appropriate treatment based on their assigned arm, the mice were followed for survival. Kaplan-Meier survival curve displaying the results is shown in FIG. 4A. Improved survival was demonstrated with combination anti-PD-1 therapy plus radiation compared with either modality alone: median survival was 25 days in the control arm, 27 days in the anti-PD-1 antibody arm, 28 days in the radiation arm, and 53 days in the radiation plus anti-PD-1 therapy arm (P<0.05 by log-rank Mantle-Cox). Long-term survival was only observed in the combined treatment arm, with a fraction (20-40%) of animals alive at day +180 post treatment. By contrast, all mice in the control arm were dead by day 28. The survival experiments have been repeated in triplicate with similar findings each time.

Bioluminescent imaging results correlated with the survival findings (FIG. 4C). Mice underwent bioluminescent imaging on day-7 post-implantation (prior to receiving any therapy), and again on day-21 post-implantation (after all therapies had been completed). On day-7, mice in all treatment groups had approximately equal bioluminescent signal. In the control mice, by day-21, all mice had stronger signal than day-7, showing tumor progression. In mice treated with either radiation or anti-PD-1 antibody alone, a heterogeneous response was observed, with some mice showing increasing bioluminescent signal, some showing stable signal, and some showing minor tumor regression. In the mice receiving both radiation and anti-PD-1, however, most mice show tumor regression with a few mice showing stable disease. PD-L1 expression in the GL261 cell line also was confirmed via western blot analysis (FIG. 4B).

Example 3

Immunologic studies. To assess the immunologic status in the brain that correlates with the different survival outcomes observed in the different treatment arms, mice were sacrificed on day-21 post-implantation. Brain/tumor, cervical lymph nodes, and spleen were harvested and assessed for their immunologic parameters via flow cytometry. Mice treated with both radiation and the immunotherapeutic agent, anti-PD-1 antibodies, had the highest number of cytotoxic T-cells (CD8+/IFNγ+/TNFα+ cells) in the brain compared to mice from the other groups, especially when normalized to tumor size (FIG. 5A). Fewer regulatory T-cells (CD4+/FOXP3+ cells) were observed in the mice receiving radiation plus anti-PD-1 antibodies (FIG. 5B). The ratio of cytotoxic to regulatory T-cells was highest in the mice receiving both radiation plus antibody (FIG. 5C).

To test for immunologic memory, mice who were "cured" of the brain tumor (alive at least 90-days post-implantation, which only occurred in the radiation+anti-PD-1 antibody arm), were re-challenged with flank-implantation of 1.5 million GL-261-luciferase cells. These "cured" mice were compared to "naïve" mice that have never been implanted with tumor nor received any treatment. FIG. 6 shows the results of the re-challenge experiments. By day-21, tumors in the "naïve" mice had reached at least 1000 mm³ in size, whereas no "cured" mice had grown any visible flank tumors. Day-10 post-flank-implantation bioluminescent imaging of flank tumors confirmed the results of tumor size measurements.

Example 4

Combining the immunotherapeutic agent anti-CTLA-4 and anti-4-1BB agonist antibodies with focused radiotherapy. As in Example 2, to establish orthotopic tumors, 130,000 GL261 glioma cells transfected with luciferase were intracranially implanted into the caudate-putamen complex of 6-8 week old C57/BL6 mice. On day 7 after implantation, mice were stratified into four treatment groups using bioluminescent imaging: (1) isotype controls (2) stereotactic radiation (3) anti-4-1BB and anti-CTLA-4 antibodies (4) stereotactic radiation with anti-4-1BB and anti-CTLA-4 antibodies (FIG. 8). Stereotactic radiation was delivered on day 10 after implantation under CT guidance on a small animal irradiator using a 3 mm beam set to 10 Gy. 0.2 mg of anti-4-1BB IP was administered on days 11, 14, and 17, and 0.8 mg of anti-CTLA-4 IP was administered on days 11, 17, and 23. IgG controls were also tested for both groups. Monoclonal antibodies were produced from hybridoma supernatant.

Example 5

Survival Analysis. Mice treated with stereotactic radiosurgery combined with anti-4-1BB and anti-CTLA-4 antibodies resulted in a significantly (P<0.05, log rank test) higher median survival than the controls and radiation with IgG isotypes (FIG. 9).

Example 6

TILs Analysis. To monitor the immune response, brains from three mice in each treatment group were harvested on day 18 to determine the numbers of CD4+ (FIG. 10A) and CD8+ cells (FIG. 10B) producing IFN-y. There is no difference in the absolute counts of TILs through the treatment groups. However, harvested brain from the radiation plus anti-4-1BB and anti-CTLA-4 group had smaller tumors. When taking tumor volumes into consideration, there is a relative higher number of CD8+IFN-y+ cells in the radiation plus anti-4-1BB and anti-CTLA-4 group.

Example 7

Protective Memory Response. Long-term survivors, considered "cured" from their brain tumors, and naïve animals were injected subcutaneous with $10^6$ GL261-LUC cells to assess a protective antitumor memory response. After tumor re-challenge, flank tumor growth was monitored for an additional 50 days. All naïve animals had palpable tumors by day 17, whereas the long-term survivors had no sign of tumor growth by day 50 (FIG. 11).

Example 8

Specificity of Memory Response. To determine whether the systemic antitumor memory response is specific for GL261 only, GL261 was compared to B16 melanoma flank tumors. Cured and naïve mice were injected subcutaneous with $10^6$ GL261-LUC cells in the left flanks and $10^5$ B16-LUC cells in the right flanks. Naïve animals had palpable tumors on both flanks; growth of GL261 and B16 tumors. However, cured animals grew only tumors on the right flanks and no tumors on the left flanks; growth of B16 tumors only (FIG. 12). The study shows that double immunotherapy using anti-4-1BB agonist and anti-CTLA-4 blockade combined with stereotactic radiosurgery results in long-term survival with development of a protective memory response.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating a tumor in a subject in need of treatment thereof, the method comprising administering to the subject a therapeutically effective dose of focused radiation selected from the group consisting of stereotactic radiosurgery and fractionated stereotactic radiosurgery, to treat the tumor in combination with at least one immune checkpoint inhibitor.

2. The method of claim 1, wherein the focused radiation has a radiation source selected from the group consisting of a particle beam (proton), cobalt-60 (photon), and a linear accelerator (x-ray).

3. The method of claim 1, wherein the at least one immune checkpoint inhibitor is one or more monoclonal antibodies.

4. The method of claim 3, wherein the monoclonal antibody is selected from the group consisting of anti-PD-1 antibody, ipilimumab (anti-CTLA-4), anti-B7-H4, anti-B7-H1, anti-LAG3, BTLA, anti-Tim3, anti-B7-DC, anti-CD160, KIR antagonist antibodies, anti-4-1BB, anti-OX40, anti-CD27, and CD40 agonist antibodies.

5. The method of claim 4, further comprising administering at least one adjuvant in combination with the at least one immune checkpoint inhibitor.

6. The method of claim 5, wherein the at least one adjuvant is selected from the group consisting of a cytokine, an interleukin, an interferon, a granulocyte-macrophage colony-stimulating factor (GM-CSF), Bacille Clamette-Guérin (BCG), a keyhole limpet memocyanin (KLH), incomplete Freund's adjuvant (IFA), QS-21, DETOX, and dinitrophenyl.

7. The method of claim 1, wherein the tumor is a tumor associated with a cancer selected from the group consisting of a cancer involving the spine, a lung cancer, a pancreatic cancer, a prostate cancer, a liver cancer, a kidney cancer, a breast cancer, a melanoma, a metastatic orbital tumor, an orbital lymphoma, a benign brain tumor, and combinations thereof.

8. The method of claim 1, further comprising administering to the subject at least one additional therapeutic agent.

9. A method of neoadjuvant therapy for treating cancer in a subject in need of treatment thereof, the method comprising:
(a) administering to the subject a therapeutically effective dose of focused radiation selected from the group consisting of stereotactic radiosurgery and fractionated stereotactic radiosurgery, in combination with a therapeutically effective first dose of at least one immune checkpoint inhibitor;
(b) performing surgery on the subject to remove at least a portion of a tumor associated with the cancer; and
(c) administering to the subject a therapeutically effective dose of focused radiation selected from the group consisting of stereotactic radiosurgery and fractionated stereotactic radiosurgery, in combination with a therapeutically effective second dose of at least one immune checkpoint inhibitor;
wherein steps (a), (b), and (c) can be repeated in series or individually as necessary to treat the cancer in the subject.

10. The method of claim 9, further comprising administering to the subject additional chemotherapy and or radiation treatment.

11. The method of claim 10, further comprising administering to the subject adjuvant therapy.

12. The method of claim 11, wherein the at least one adjuvant is selected from the group consisting of a cytokine, an interleukin, an interferon, a granulocyte-macrophage colony-stimulating factor (GM-CSF), Bacille Clamette-Guérin (BCG), a keyhole limpet memocyanin (KLH), incomplete Freund's adjuvant (IFA), QS-21, DETOX, and dinitrophenyl.

13. The method of claim 9, further comprising administering to the subject at least one additional immune checkpoint inhibitor.

14. The method of claim 9, wherein the at least one immune checkpoint inhibitor is selected from one or more monoclonal antibodies.

15. The method of claim 14, wherein the monoclonal antibody is selected from the group consisting of anti-PD-1 antibody, ipilimumab (anti-CTLA-4), anti-B7-H4, anti-B7-H1, anti-LAG3, BTLA, anti-Tim3, anti-B7-DC, anti-CD160, KIR antagonist antibodies, anti-4-1BB, anti-OX40, anti-CD27, and CD40 agonist antibodies.

16. The method of claim 9, wherein the tumor is a tumor associated with a cancer selected from the group consisting of a cancer involving the spine, a lung cancer, a pancreatic cancer, a prostate cancer, a liver cancer, a kidney cancer, a breast cancer, a melanoma, a metastatic orbital tumor, an orbital lymphoma, a benign brain tumor, and combinations thereof.

* * * * *